(12) United States Patent
Koch (10) Patent No.: US 11,918,520 B2
(45) Date of Patent: Mar. 5, 2024

(54) SURGICAL ROTATIONAL UNIT WITH IMPROVED ROTATIONAL LOCKING

(71) Applicant: MAQUET GMBH, Rastatt (DE)

(72) Inventor: Guido Koch, Karlsruhe (DE)

(73) Assignee: MAQUET GMBH, Rastatt (DE)

( * ) Notice: Subject to any disclaimer, the term of this patent is extended or adjusted under 35 U.S.C. 154(b) by 1031 days.

(21) Appl. No.: 16/613,694

(22) PCT Filed: May 17, 2018

(86) PCT No.: PCT/EP2018/062944
§ 371 (c)(1),
(2) Date: Jul. 24, 2020

(87) PCT Pub. No.: WO2018/211017
PCT Pub. Date: Nov. 22, 2018

(65) Prior Publication Data
US 2020/0360215 A1    Nov. 19, 2020

(30) Foreign Application Priority Data

May 17, 2017    (DE) ...................... 10 2017 110 719.3

(51) Int. Cl.
*A61G 13/00* (2006.01)
*A61B 90/14* (2016.01)
*A61G 13/10* (2006.01)
*A61G 13/12* (2006.01)

(52) U.S. Cl.
CPC ............ *A61G 13/125* (2013.01); *A61B 90/14* (2016.02); *A61G 13/0081* (2016.11);
(Continued)

(58) Field of Classification Search
CPC ......... A61B 90/14; A61B 90/16; A61B 90/17; A61B 90/18; A61B 90/50; A61B 90/57;
(Continued)

(56) References Cited

U.S. PATENT DOCUMENTS

| 4,516,519 A | 5/1985 | Gulick |
| 10,072,793 B2 | 9/2018 | Wysluch et al. |

(Continued)

FOREIGN PATENT DOCUMENTS

| DE | 102012112716 A1 | 6/2014 |
| DE | 102014108745 A1 | 12/2015 |

(Continued)

OTHER PUBLICATIONS

International Search Report dated Jul. 25, 2018 during the prosecution of corresponding PCT application No. PCT/EP2018/062944, 2 pages.
Notification of Reasons for Refusal dated Jun. 28, 2022 during the prosecution of corresponding Japan application No. 2019-563562, 4 pages.
Search Report mailed in German Published Application No. dated Jan. 31, 2018.

*Primary Examiner* — Adam Baker (57) ABSTRACT

Rotation unit (16) for connecting to an operating table for rotation of a patient's leg about its longitudinal axis, wherein the rotation unit (16) comprises: an interface (24) for attachment of the foot of the patient's leg on the rotation unit (16); a rotor, to which the interface (24) is connected in a torsionally resistant manner and which is used for rotation of the interface (24) and thus of the patient's leg about the longitudinal axis; a stator (42), on which the rotor is rotatably mounted, such that the rotor can rotate relative to the stator; a rotary handle (22) for rotation of the rotor; and a locking assembly (26) for blocking the rotation of the rotor relative to the stator. The locking assembly (26) can be actuated by means of an action on the rotary handle.

15 Claims, 5 Drawing Sheets

(52) U.S. Cl.
CPC ....... *A61G 13/101* (2013.01); *A61G 13/1295* (2013.01); *A61G 2200/327* (2013.01); *A61G 2210/10* (2013.01)

(58) Field of Classification Search
CPC ......... A61B 90/25; A61B 90/11; A61B 90/30; A61B 2090/57; A61B 2090/571; A61F 5/37; A61F 5/3761; A61F 5/3769; A61F 5/3792; A61G 7/065; A61G 7/075; A61G 7/0755; A61G 7/1082; A61G 7/1096; A61G 7/109; A61G 13/125; A61G 13/1245; A61G 13/124; A61G 13/1235; A61G 13/123; A61G 13/0081; A61G 13/1295
USPC ............................................................ 5/624
See application file for complete search history.

(56) References Cited

U.S. PATENT DOCUMENTS

| | | |
|---|---|---|
| 2013/0191994 A1 | 8/2013 | Bellows et al. |
| 2015/0366622 A1* | 12/2015 | Wyslucha ............. F16D 41/105 5/648 |
| 2016/0151224 A1 | 6/2016 | Ferro et al. |

FOREIGN PATENT DOCUMENTS

| | | |
|---|---|---|
| JP | H11511231 A | 9/1999 |
| JP | 2013009603 A | 1/2013 |
| JP | 2015504766 A | 2/2015 |
| WO | 9707447 A1 | 2/1997 |
| WO | 2013034916 A1 | 3/2013 |
| WO | 2013112879 A1 | 8/2013 |

* cited by examiner

SURGICAL ROTATIONAL UNIT WITH IMPROVED ROTATIONAL LOCKING

AREA OF THE INVENTION

The present disclosure relates to an operating table and the accessories thereof, including those in the area of orthopedic surgery, particularly orthopedic extension.

DESCRIPTION OF THE PRIOR ART

The present disclosure relates generally to surgical rotation assemblies. A rotation assembly in the form of a spindle traction mechanism 210 is known from international patent application WO 2013/034916 A1, filed by Malcolm Wootton; see FIG. 18 and page 22 of the description for more information. Such spindle traction mechanisms are used with certain surgical interventions, as is described in the following.

When operating on patients, it is often necessary that parts of the patient, particularly limbs, must be secured and moved in a precise manner. Particularly with operations in which the position of a body part must be precisely changed multiple times, adjustable treatment devices are necessary. Thus, with orthopedic interventions such as, e.g., a prosthetic hip procedure according to the direct anterior approach as well as with total hip arthroplasty, the patient's leg must be supported in a freely accessible manner and rotated repeatedly.

In this case, the patient's leg is tensioned in a traction unit in a straight, self-supporting manner. Such traction units are also characterized as extension devices in connection with operating tables. These extension devices comprise at least one extension bar, which can be connected on its one end to the operating table via an interface and which has a bracket for the traction unit on its other end. The extension bar can be connected to a patient support surface of the operating table or attached thereto.

To that end, the patient's foot is placed in a so-called extension shoe, to the sole of which a spindle traction mechanism, such as the one described by Wootton, is adapted. A tractive force can be applied in the longitudinal direction of the leg via this spindle traction mechanism in order, for example, to place the fractured edges of the bone into their original position during the repositioning. In addition, it should be possible to pivot the leg inward and outward about its longitudinal axis. To do this, the angle of rotation of the leg must be changed multiple times according to the surgical workflow and the medical necessity. The maximum typical range of rotation is ±180°.

In order to change the angle of rotation of a patient's leg, which is tensioned via the spindle traction mechanism as per Wootton, an operator must manipulate a rotatable rotor, which is accommodated in a stator formed as a clamp, by means of a handle 269. In doing so, the operator must turn a clamping lever 268 with one hand to unblock the rotation such that the rotation of the patient's leg is unblocked by means of the extension device. Subsequently, the operator rotates the patient's leg about its longitudinal axis into the desired position. In doing so, the patient's toe can be used as an indicator of the angle of rotation about the longitudinal axis. The patient's leg then must be manually held in the desired angle of rotation with one hand, while a reset force acts in the direction opposite the implemented rotation. For locking, the clamping lever 268 is then pulled with the other hand such that the patient's leg is secured in the desired angle of rotation by the extension device. In order to place the patient's leg in a different angle of rotation, the operator must release the handle 269 with one hand under high load application in order to again turn the clamping lever 268 and again rotate the patient's leg into the desired position in a controlled manner. Subsequently, the clamping lever 268 is again secured with one hand.

In practice, it is known that this procedure must be repeated multiple times during an operation. In the explained sequence, the acts of releasing/tightening the clamping lever 268 and rotating/holding the patient's leg in the desired position are sometimes implemented simultaneously. In doing so, the effort to reset the patient's leg into a defined position is often difficult and leads to a significant strain on the operator, because significant hand strength and concentration are required for one-handed coordination of the required work steps.

Thus, sensitive positioning of the patient's leg is only possible to a limited extent during an operation, such that there is a risk of an undesired adjustment of the angle upon rotation of the patient's leg or upon an insufficient securing of the clamping lever 268 for the patient. In order to minimize this risk, it is customary that one person turns the clamping lever 268, while a second person places the patient's leg into the desired position and holds it there until the clamping lever 268 is again locked. The effort and the costs incurred are relatively high for this with two people. Furthermore, the risk of contamination increases during the procedure.

A further spindle traction mechanism is known from document DE 10 2014 108 745 A1. With this one, there is a locking assembly, which is actuated in that the provided rotary handle is rotated into one of the two directions of rotation.

Document DE 10 2012 112 716 A1 describes a medical retaining arm comprising at least one joint with two joint bodies, which can be rotated opposite each other about an axis of rotation, wherein a first of the joint bodies has multiple locking pins and a second of the joint bodies has multiple locking recesses, and wherein the number of locking pins is different from the number of locking recesses.

SUMMARY OF THE DISCLOSURE

The present disclosure relates, inter alia, to rotation assemblies, extension bars with rotation assemblies, operating tables with rotation assemblies, operating tables with extension bars and rotation assemblies, as well as a method for using rotation assemblies during surgical interventions.

An object of the present disclosure is to provide a rotation assembly, with which the rotating and locking of a patient's leg can be handled safely and comfortably by a user, even under high load applications.

The present disclosure relates to a rotation assembly for connecting to an operating table for the purpose of rotating a patient's leg around its longitudinal axis, wherein the rotation assembly has all or a part of the following features:
   an interface for attaching the foot of the patient's leg to the rotation assembly;
   a rotor, to which the interface is connected in a torsionally resistant manner and which is used to rotate the interface and thus the patient's leg about the longitudinal axis;
   a stator, on which the rotor is rotatably mounted, such that the rotor can rotate relative to the stator;
   a rotary handle for rotating the rotor; and
   a locking assembly for blocking the rotation of the rotor relative to the stator, wherein the rotary handle is mounted on the rotor so as to move, and wherein the locking assembly is actuated by means of moving the rotary handle on the rotor.

Due to the fact that the locking assembly can be actuated by means of an action on the rotary handle, the user can loosen the locking assembly, rotate the patient's leg, and retighten the locking assembly, without having to take hands off of the rotary handle. The user can leave both hands on the rotary handle during the entire process for rotating the patient's leg and operate the locking assembly without outside help. In this manner, the rotating and locking of the patient's leg can be realized comfortably by a single person.

The rotary handle is used to set a desired angle of rotation and to actuate the locking assembly. According to some embodiments, the rotary handle can be coupled to the rotor in a torsionally resistant manner.

The locking assembly may comprise at least two groups of locking pins and a plurality of locking recesses, wherein the number of locking pins is different from the number of locking recesses. The at least two groups of locking pins and a plurality of locking recesses may be distributed on the circumference of the locking assembly. The locking recesses may be evenly distributed about the entire circumference of the stator with an adjustment range of ±180°. The releasing and blocking of a rotational movement of the rotor can also take place even under high load applications by means of the locking assembly with at least two groups of locking pins and a plurality of locking recesses different therefrom. This locking assembly can be used, for example, to block the rotation of an extremity tensioned via the rotation assembly. With other operating techniques, even a free rotation can take place under user-friendly conditions. Further medical and nonmedical application areas should not be excluded.

Furthermore, the locking recesses of the present locking assembly, said recesses being formed on the stator, have an angle division defined in advance. In doing so, the angle division of the locking pins of the respective group of the at least two groups of locking pins differs from the angle division of the locking recesses by a difference angle α. The number of locking pins in this case should be measured such that the angular sector of the locking pins results in an even-numbered multiple of the angle division of the locking recesses. Thus, a multitude of engaging or locking positions, which are distributed over 360°, is obtained for the locking assembly. One locking pin of the respective group of the at least two groups of locking pins is positioned opposite one locking recess with each locking position. The angular distance between two locking positions is equal to the difference angle α.

According to one embodiment, the rotational movement of the rotor relative to the stator can be blocked if no axial actuation force is being exerted onto the rotary handle for the purpose of release. To do this, one of the locking pins from each group of the at least two groups of locking pins, which is precisely opposite one locking recess, enters this recess directly with its one end. If the at least two groups of locking pins are arranged at angular distances which are a multiple of the angle division of the locking recesses, one of the locking pins of the respective group of the at least two groups of locking pins thus engages simultaneously. All further locking pins of the at least two groups of locking pins, which do not make contact with a locking recess, cannot engage. The locking with multiple locking pins simultaneously, which belong to another group of locking pins, has an especially positive effect on the load capacity and stability of the locking assembly at high torques. The locking assembly ensures secure blocking of the rotation of the rotor.

Furthermore, the present locking assembly enables an unblocking of the rotational movement of the rotor. The rotation of the rotor can be unblocked by means of a simultaneous release of all locking pins. The release can be implemented by means of the axial movement of the rotary handle. For example, the rotary handling this case can be pulled back in a direction facing away from the patient such that the operator is given the opportunity to rotate the patient's leg.

The present locking assembly ensures improved operator ergonomics. In particular, clamping or securing elements that must be actuated separately can be dispensed with. Thus, an exact positioning of the rotor and a setting of the desired angle of rotation can be ensured simultaneously by means of a rotary handle.

The simple construction and comfortable operation of the locking assembly enable the operator to adjust, block, and unblock the rotor without having to release the rotary handle and be dependent on outside help.

According to some embodiments, the locking pins of the at least two groups of locking pins may be distributed on the inner circumference of the rotor. For example, the rotor may have multiple through-holes or other types of recesses on the inner circumference to accommodate the locking pins. The locking pins may be axially aligned in the respective recesses. A radial alignment of the locking pins in the respective recesses is also possible, however. This arrangement of the at least two groups of locking pins ensures increased safety and load-bearing capacity of the locking assembly in a locked state of the rotor. In addition, the functional components of the locking assembly such as, for example, the locking pins and elements having the locking recesses, can be exchanged. This enables a new alignment of the locking pins.

The locking pins of the at least two groups of locking pins may be spring-loaded in the rotor and pretensioned in the direction of the locking recesses. The spring preload additionally increases the stability of the locking assembly. Furthermore, the spring preload can be infinitely adjusted for the purposes of a reliable and complete engagement of the respective locking pins.

According to one embodiment, the at least two groups of locking pins and the locking recesses may form at least one circular assembly. This means that the locking pins and the corresponding locking recesses may be arranged concentrically, in the cross-section along at least one imaginary circular line, about the axis of rotation of the rotation assembly.

In some embodiments, the at least two groups of locking pins and the locking recesses may be arranged symmetrically radially. The respective arrangements may extend, for example, radially and/or axially. Furthermore, the arrangements of the at least two groups of locking pins and the locking recesses have the same radius. In some arrangements, the at least two groups of locking pins and the locking recesses may be distributed over the circumference of the rotor and/or stator.

The blocking must be released in order to adjust a rotor locked in a certain position. The release of the locking assembly can be achieved by completely pulling the locking pins out of the opposing locking recesses. In doing so, the respective, engaged locking pins of the at least two groups of locking pins may be simultaneously pulled, for example, against the spring preload being exerted. Due to this release mechanism, the rotor can be quickly repositioned without extensive effort. The release may take place, for example, by means of the movement of the rotary handle along the axis of rotation of the rotation assembly.

In one of the embodiments, the rotary handle may be present as a star-shaped handle. This design should only be considered an example, however. Thus, the handle may also have a different shape, e.g. that of at least one control lever.

Furthermore, the rotary handle may be attached to a sliding sleeve and be pushed together with said sleeve. The sliding sleeve may additionally comprise an angle scale, which simplifies an exact positioning of the patient's leg. In the locked state, the sliding sleeve may be pressed against the stator with spring pressure and arranged opposite the rotor in a torsionally resistant manner. This can be achieved with the help of at least two rows of balls, which are arranged in corresponding axial tracks between the rotor and the sliding sleeve, which roll off in the axial direction, and which allow no movement in the radial direction.

The locking pins may be formed such that their engaging parts settle gently into the respective locking recesses during a rotational movement and thus only cause a slight amount of friction. In this case, the respective end sections of the locking pins may be nonuniform, for example flattened, round, elliptical, crowned, or spherical, and have various irregularities, such as protrusions or recesses.

The engaged locking pins may have at least two sections. In a locked state of the locking assembly, a first section of an engaged locking pin is then located in a corresponding locking recess formed on the stator, wherein a second section of the engaged locking pin protrudes radially over the respective locking recess.

The sliding sleeve may have a release element in the form of a collar on the stator-side end, said release element protruding into the area of the pins but having no contact with the pins in the standby position. According to some embodiments, the release element may be formed as a release ring, which is formed such that it has contact with the locking pins of the at least two groups of locking pins during movement of the rotary handle along the axis of rotation. The release element in this case may have contact with the second protruding section of the respective locking pins. Furthermore, the release element may be in the form of a tube, a collar, or an irregular protrusion.

The present rotation assembly may be formed such that the rotor is rotatably mounted in the stator but does not move axially. In doing so, the rotor may enclose a pullout, which is formed so as to move axially relative to the rotor and in a torsionally resistant manner. This is achieved by two cylindrical pins on the end of the rotor facing the patient, which engage in corresponding recesses on the pullout. The pullout may, accordingly, slide along the cylindrical pins, while the torque to be transferred is supported thereon. Because the hard-coated guiding surfaces of the pullout are exposed, it is positioned by means of sliding bearings in the rotor, which are suitable for dry operation. With some embodiments, the cylindrical pins are formed from plastic due to high edge pressure on the surface of the pullout.

The present rotation assembly may be formed such that the locking assembly can be locked in a release position In doing so, the rotary handle may have a button, which is used to lock the rotor in a release position. The locking of the rotor in a release position results in the ability of the rotation assembly to rotate freely. In doing so, other mechanisms may also be used such as, for example, pushbuttons, locking pins, or switches attached to the stator, provided they are suitable for ensuring the desired release. The button can be actuated without having to release the rotary handle. Actuation of the button can also take place with remote control.

The present locking assembly may also be sustainably released by means of the actuatable button in order to give the operator the possibility of freely manipulating the patient's leg. For example, to do this, the operator can pull the sliding sleeve towards himself, as previously described, by means of the rotary handle, then press the locking button, and release the traction. The button thus remains in the pressed position and keeps the sliding sleeve from falling back into the locked position. In order to again lock the rotation, traction is again exerted on the sliding sleeve. Thus, the button is released, and the rotor is locked.

The locking assembly may be formed such that the number and division of the adjacent locking pins of the at least two groups of locking pins and the number of corresponding locking recesses are different. The respective ratio between the locking pins and the locking recesses of the locking assembly result from the angle difference selected beforehand. Consequently, the number of locking pins of the at least two groups of locking pins may be greater than the number of locking recesses. According to further embodiments, the number of locking recesses may be greater than the number of locking pins of the at least two groups of locking pins.

The locking assembly may be formed such that the rotor comprises at least two groups of locking pins. In order to lock the rotational movement of the rotor, one of the locking pins of the at least two groups of locking pins may be accommodated with one section completely in one of the locking recesses. For example, the rotor may comprise four groups of locking pins, wherein, in order to block the rotational movement of the rotor, one of the locking pins of the four groups of locking pins is accommodated with one section completely in one of the locking recesses.

Depending on the design of the locking assembly, the number of locking pins within the at least two groups of locking pins and locking recesses may also vary. The locking assembly may have, for example, four groups of locking pins with six locking pins per group on the circumference of the rotor, wherein the regular angle division of the locking pins is 12°. Furthermore, this embodiment 25 comprises corresponding locking recesses on the contact surface of the stator, which are distributed in a circle on the complete circumference at intervals of 14.4°. Because the four groups of locking pins are spaced apart from one another by a multiple of 14.4°, one locking pin from each group of locking pins engages simultaneously upon locking. Furthermore, upon a rotation of 2.4°, the next set of locking pins may engage; this corresponds to the difference in the two divisions. This results in a precise, practically infinite engagement, which is substantially less than the division of the locking pins.

BRIEF DESCRIPTION OF THE DRAWINGS

Exemplary embodiments of the present disclosure will be described in the following with reference to the appended drawings, in which the same reference numerals characterize the same or corresponding elements in each case.

DETAILED DESCRIPTION

Exemplary embodiments of the present disclosure will be described in the following description with reference to the drawings. The drawings in this case are not necessarily true-to-scale but are intended to merely schematically illustrate the respective features.

In doing so, it should be noted that the following described features and components can each be combined with one another regardless of whether they have been described in connection with one single embodiment. The combination of features in the respective embodiments is only an illustration of the basic construction and function of the claimed device.

Figure 1:
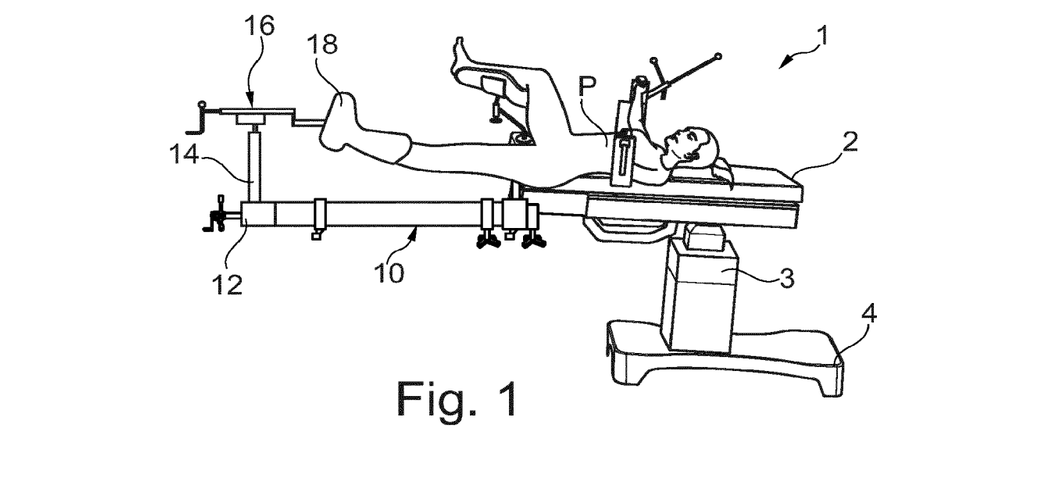
FIG. 1 shows a representation of an operating table with an extension bar, with which a rotation assembly in the form of a spindle traction mechanism can be used with a locking assembly according to an embodiment of the present disclosure.

As shown in FIG. 1, an operating table 1 comprises a patient support surface 2, a column 3, and a base 4. In order to implement orthopedic operations, an extension bar 10 can be used, by means of which the leg of the patient P can be secured in a desired position. To this end, a moveable strut 14 can be attached to a bar 12 of the extension bar 10, said strut then supporting a spindle traction mechanism 16, which is connected to a bracket 18 for a patient's foot. When the movable strut 14 is secured in a suitable position on the bar 12, traction can be applied to the patient's foot in a direction along the longitudinal axis L of the spindle traction mechanism 16, via the spindle traction mechanism 16, in order to pull apart, for example, a hip joint of the patient P.

Figure 2:
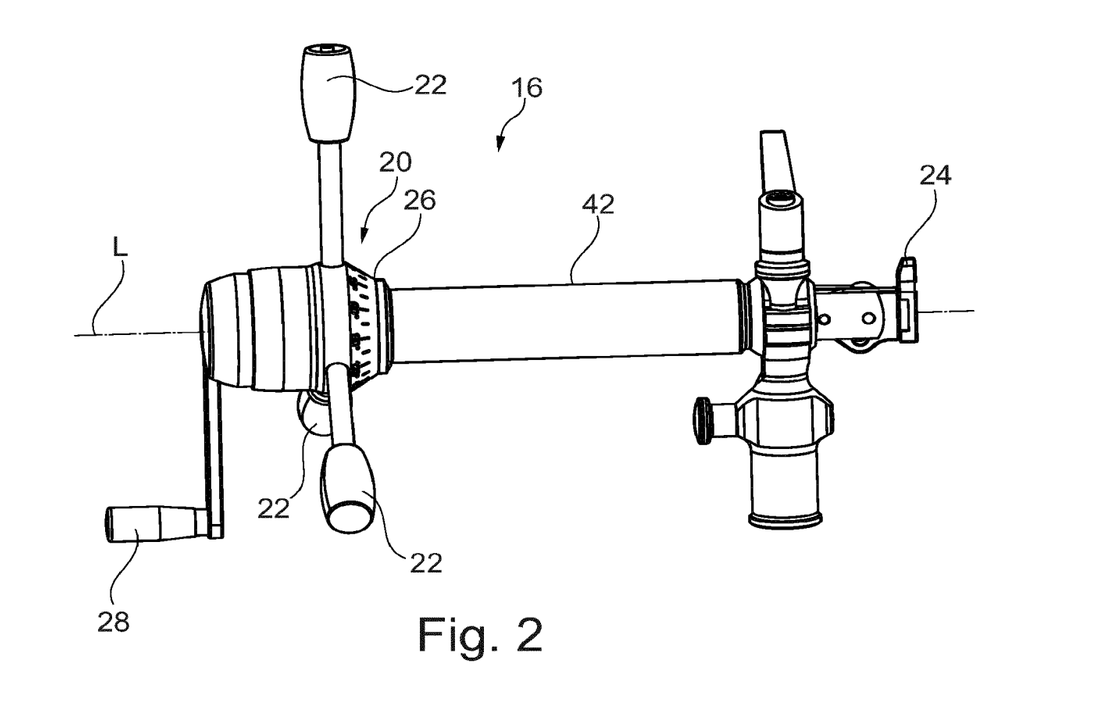
FIG. 2 shows a spindle traction mechanism with a locking assembly according to an embodiment of the present disclosure.
Figure 3:
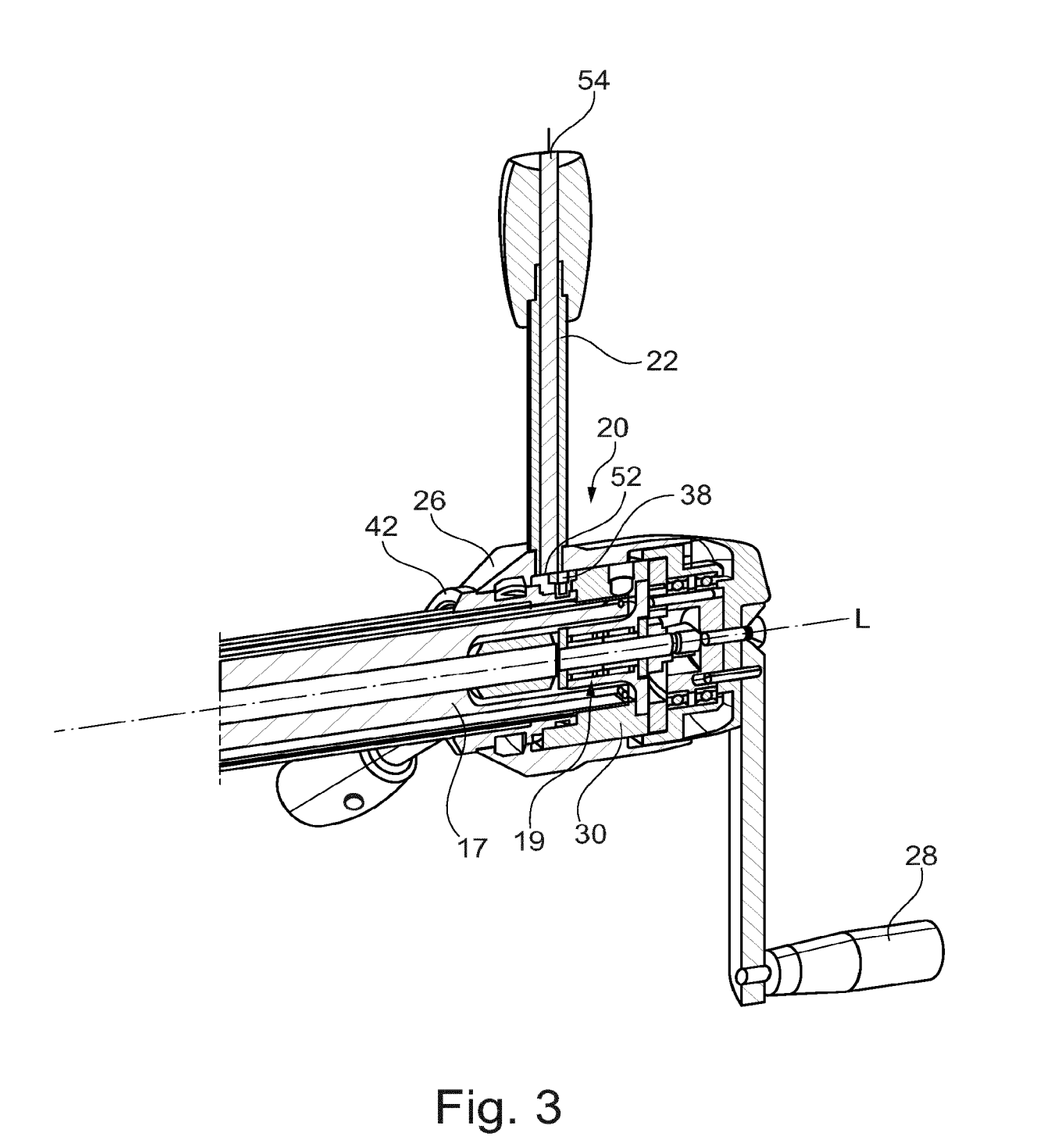
FIG. 3 is a longitudinal section through the rear part of the spindle traction mechanism from FIG. 2.

As shown in FIGS. 2 and 3, a locking assembly 20 according to an embodiment of the present disclosure can be attached to such a spindle traction mechanism 16. The spinal traction mechanism 16 comprises a star-shaped handle 22, with which a user can rotate the interface 24 of the spindle traction mechanism 16 about a longitudinal axis L of the spindle traction mechanism 16. Thus, a patient's leg tensioned in a bracket 18 (see FIG. 1) by means of the spindle traction mechanism 16 can be pulled axially along the longitudinal axis L, on one hand, by actuating a handcrank 28, which is coupled to a traction spindle 17 of a spindle drive 19, and can be rotated about the longitudinal axis L, on the other hand, by actuating the star-shaped handle 22. A scale ring 26 in the form of a sliding sleeve in this case indicates the set angle of rotation. The spindle drive 19 has an outer thread, which executes the rotation of the handcrank 28 in a longitudinal shift.

The arms of the star-shaped handle 22 extend outward radially, starting from the sliding sleeve 26. The sliding sleeve 26 can be moved back and forth along the longitudinal axis L. In doing so, the sliding sleeve 26 encloses a rotor-stator unit 30, 42, upon which the sliding sleeve is mounted so as to slide. The rotor-stator unit comprises a rotor (rotatable bushing) 30 as well as a stator (stationary hub) 42. The rotor 30 is rotatably mounted on the stator 42. Thus, the rotor 30 can rotate about the longitudinal axis L relative to the stator 42.

As shown in FIG. 3, both the rotor 30 and the stator 42 are each formed as a cylindrical sleeve. These two sleeves enclose a section of the spindle drive 19. The rotor 30 and the stator 42 are situated one after the other in the direction of the longitudinal axis L. In this case, the stator 42 is used closer to the patient's leg than the rotor 30.

In the embodiment shown, the star-shaped handle 22 is coupled to the rotor 30 via the sliding sleeve 26 in a torsionally resistant manner but is moveable on the rotor in the axial direction. Under a spring load, the star-shaped handle 22 is retained in this case in its front position (facing the patient P), which is shown in FIGS. 2 and 3.

The rotor 30 is locked in this position. For adjustment, the user standing at the foot and must pull the star-shaped handle 22 a few mm towards himself. This will release the lock, which is described further below in connection with FIGS. 4-6, and the rotor 30 can be freely positioned. If the user releases the star-shaped handle 22 and/or releases the axial traction, the spring force then moves the star-shaped handle 22 back in the direction of the patient, into the starting position shown in FIG. 2, and the rotor 30 is locked. In this case, the user can keep both hands on the star-shaped handle 22 and, in doing so, release the locking assembly 20, adjust the angle of rotation of the patient's leg, and subsequently again lock the locking assembly 20 by releasing the axial traction on the star-shaped handle 22, without having to release the star-shaped handle 22 itself. Thus, the user can precisely position and guide the patient's leg.

Figure 4:
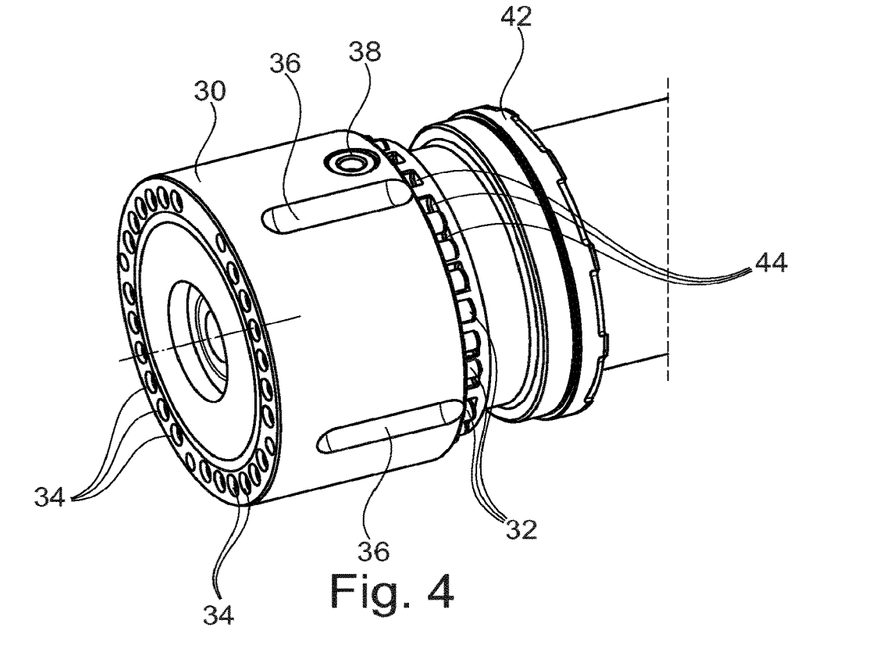
FIG. 4 shows a few components of the locking assembly of the spindle traction mechanism from FIG. 2.

FIG. 4 shows the rotor 30 of the locking assembly 20 from FIG. 2, wherein a plurality of locking pins 32 are accommodated in through-holes 34 in the rotor 30. A stator 42 has a plurality of locking recesses 44, in which the locking pins 32 can optionally engage. Furthermore, guiding grooves 36 can be seen in FIG. 4, by means of which the axial movement can be guided between the star-shaped handle 22 and the scale ring/sliding sleeve 26 connected thereto, on one hand, and the rotor 30, on the other hand. A locking bush 38 on the rotor is used to lock the star-shaped handle 22 in an unlocked setting of the locking assembly 20, as described in detail below.

Figure 5:
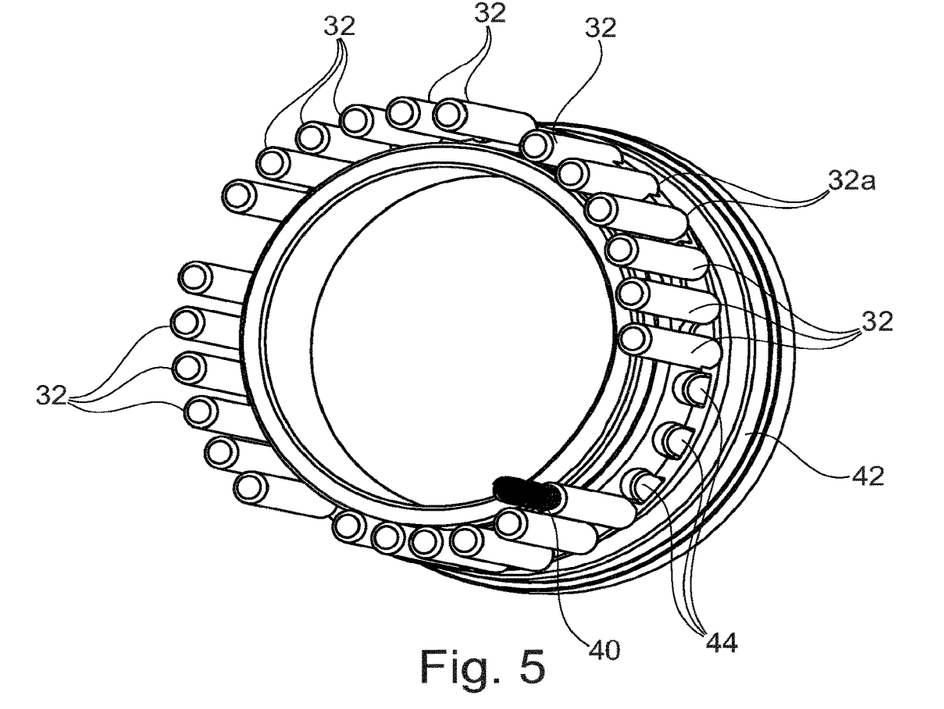
FIG. 5 shows locking pins and locking recesses of the locking assembly of the spindle traction mechanism from FIG. 2.

FIG. 5 shows the locking pins 32 mounted in the rotor 30 (see FIG. 4), wherein each locking pin 32 is pretensioned in the stator 42 in the direction of the locking recesses 44 via an assigned spring 40. In this case it can be seen that the number and distribution of the locking pins 32 about the circumference of the rotor 30 is not the same as the number and distribution of the locking recesses 44 on the stator 42. In the example shown, the locking pins 32 are divided into four groups of six locking pins 32 per group, in the shape of a ring, about the circumference of the rotor 30, wherein a distance between adjacent groups of locking pins 32 is greater than between adjacent locking pins 32 within a group. The total of 25 latching recesses 44 in the example shown are uniformly distributed about the circumference of the stator 42.

According to other embodiments however, different numbers of locking pins 32 and locking recesses 44 are conceivable per group and per rotor and/or stator, as long as it is assured that the number and/or the angular distance of the locking pins 32 differs from the number and/or from the angular distance of the latching recesses 44.

Thus, a total of 8 to 60 locking pins may be provided for each application case. In doing so, 4 to 10 pins can be combined into one group. The number of locking pin groups may be from 2 to 6. The total number for the locking recesses may vary from 9 to 61.

Due to the different number of locking pins 32 and locking recesses 44, a locking pin 32 from one group is precisely opposite a locking recess 44 and is pressed into the locking recess 44 by means of spring preload, once a very small difference angle has been exceeded. Due to the relatively high number of locking pins 32 and locking recesses 44 with the present embodiment, and due to the rotation-symmetrical arrangement of the groups of locking pins 32, precisely one locking pin 32 in each group is positioned precisely opposite one locking recess 44 and engages it. Due to the simultaneous engagement of four locking pins 32 with the embodiment shown, large retention forces can thus be achieved by means of the locking assembly 20.

The previous description shows that the locking assembly 20 comprises the locking pins 32, the locking recesses 44, as well as the sliding sleeve 26.

FIG. 5 shows that a radially external section 32a of the end face of each locking pin 32 protrudes over an end face of the corresponding locking recess 44. This radially external section 32a can have contact with a release ring 50 (see FIG. 6) when the star-shaped handle 22 is pulled back in the axial direction such that, upon an axial movement of the star-shaped handle 22, all locking pins 32 are pulled out of the locking recesses 44 and the rotor 30 is thus freely rotatable relative to the stator 42.

Figure 6:
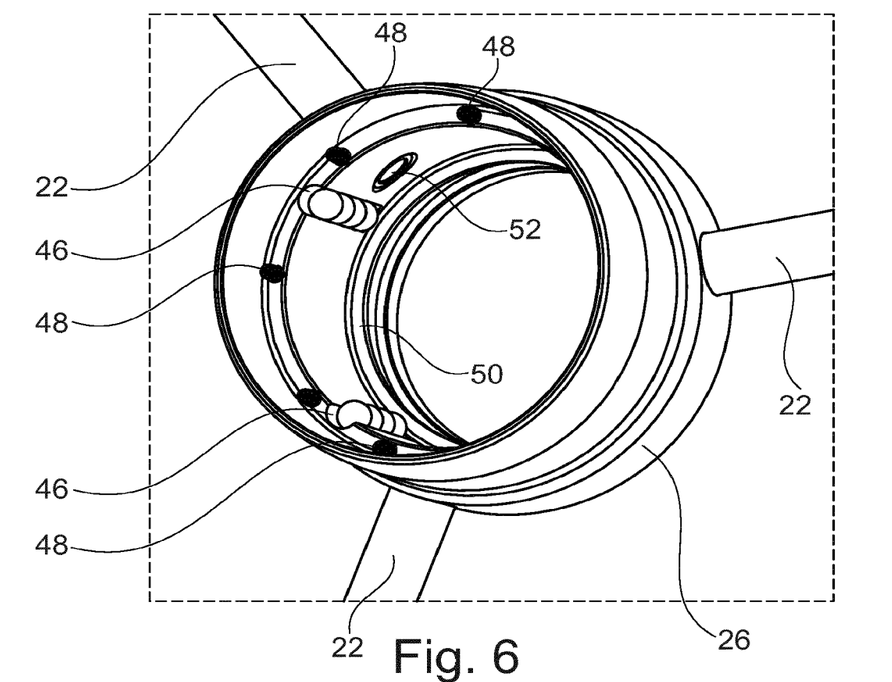
FIG. 6 shows further components of the locking assembly of the spindle traction mechanism from FIG. 2.

FIG. 6 shows the star-shaped handle 22, which is attached to the scale ring 26 and, together therewith, can be moved in the axial direction relative to the rotor 30. Bearing elements, such as, for example, the ball bearings shown, are accommodated in guide grooves 46 on the inner circumference of the scale ring. The bearing elements engage the assigned guide grooves 36 on the rotor 30 (see FIG. 4). Via springs 48, the scale ring 26 is pretensioned in the direction of a locking position of the locking assembly 20, in which one locking pin 32 from each group engages a locking recess 44.

With the embodiment shown, a circumferential protrusion 50 is provided on the inner circumference of the scale ring 26, said protrusion acting as a release ring 50 and having contact with the radially external sections 32 of the locking pins 32, and with the protrusion pulling the locking pins 32 out of the locking recesses 44 upon a movement of the star-shaped handle 22 in the axial direction along the rotor 30. However, it is also conceivable to provide the release ring 50 as a separate component, which is connected to the star-shaped handle 22 and/or the scale ring 26.

FIG. 6 further shows a stop pin 52, which is arranged in one of the radially aligned handholds of the star-shaped handle 22, and which can engage with the locking bush 38 on the rotor (see FIG. 4) in a pulled-back position of the star-shaped handle 22, in which the locking pins 32 are pulled from the locking recesses 44 by the release ring 50. Thus, the star-shaped handle 22 can be locked in a release position of the locking assembly 20. In this locked release position, the rotor 30 can be rotated freely relative to the stator 42, without permanent traction having to be exerted on the star-shaped handle 22 in the axial direction.

Figure 7:
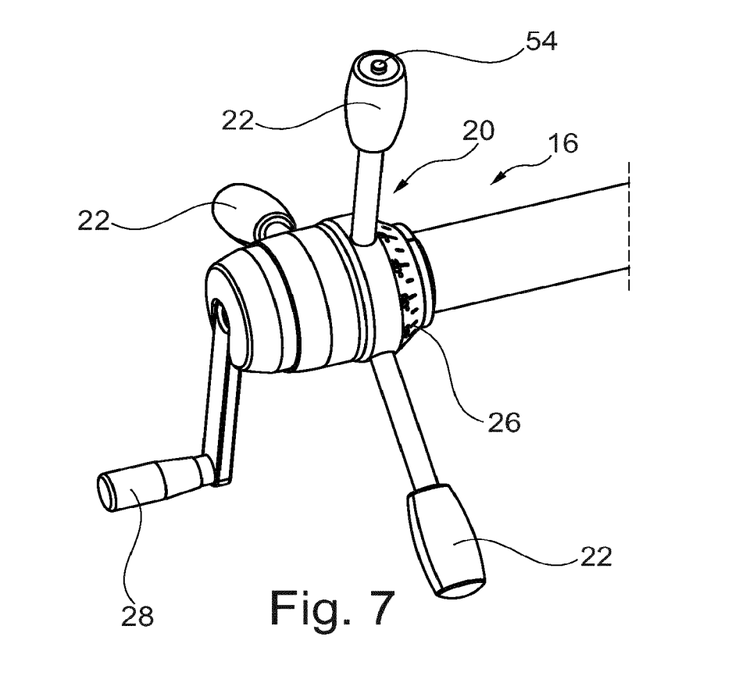
FIG. 7 shows a detailed view of the spindle traction mechanism from FIG. 2.

The actuation of the stop pin 52 in this case can take place via a pushbutton 54 on one end of a handhold of the star-shaped handle 22 (see FIG. 7). When the user pulls the star-shaped handle 22 out of the locked position of the locking assembly 20 in the axial direction toward the handcrank 28, and then actuates the pushbutton 54 in the unlocked position, the star-shaped handle 22 is then prevented from falling back into the locked position.

Another pull on the star-shaped handle 22 releases the pushbutton 54, and the locked position can be resumed, in which one locking pin 32 from each group of locking pins engages with one locking recess 44 and thus the rotation of the rotor 30 is blocked relative to the stator 42.

Figure 8:
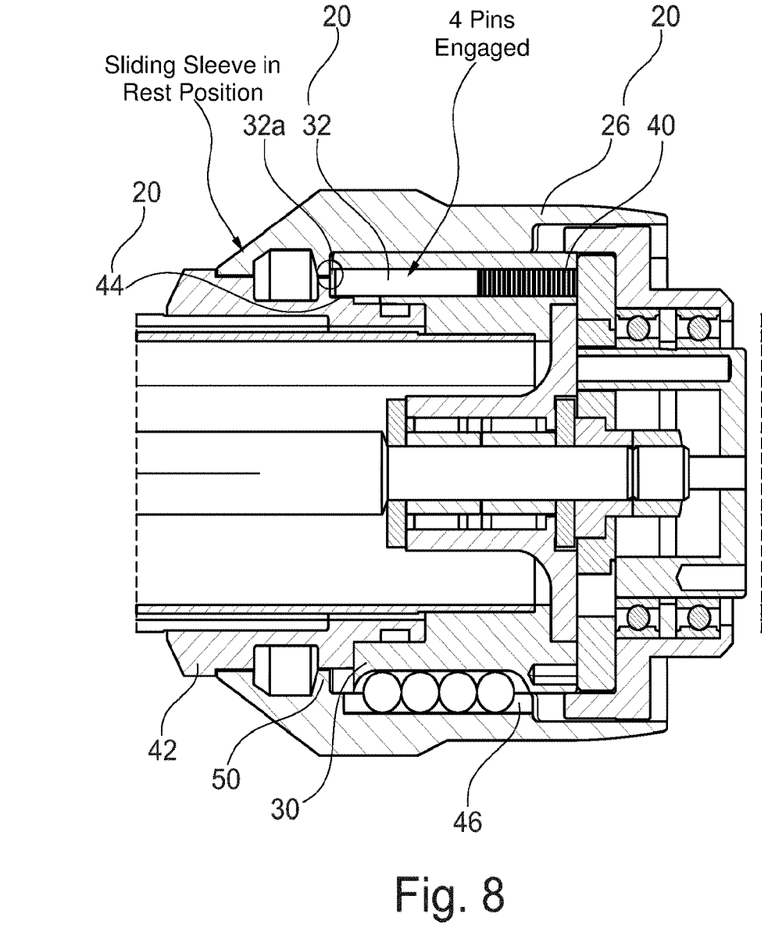
FIG. 8 shows the locking assembly of the spindle traction mechanism from FIG. 2 in a longitudinal section in the locked state.
Figure 9:
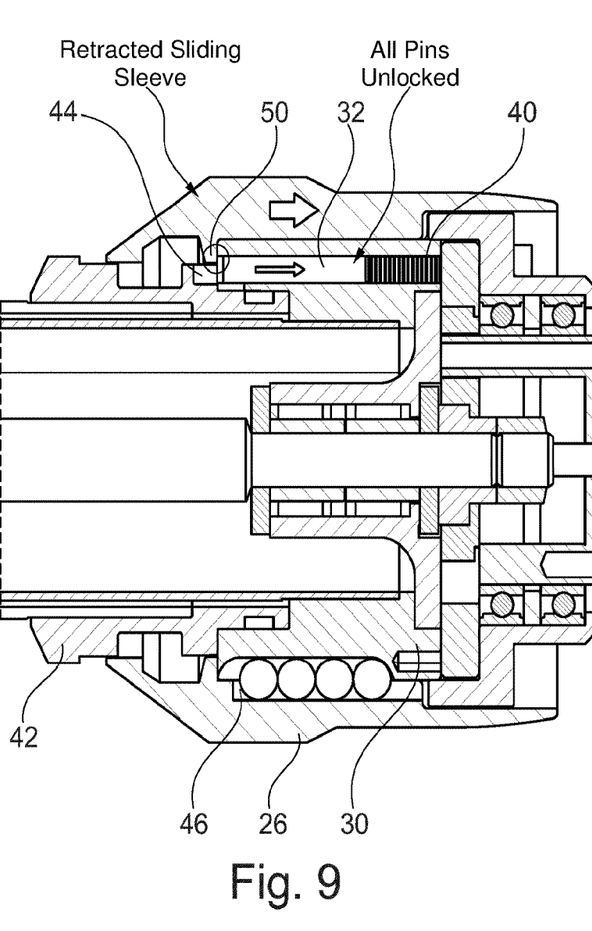
FIG. 9 shows the locking assembly of the spindle traction mechanism from FIG. 2 in a longitudinal section in the unlocked state.

FIGS. 8 and 9, which show the function of the locking assembly 20, will now be addressed. FIG. 8 shows the locked state of the locking assembly, in which the rotor 30 is locked. FIG. 9 shows the unlocked state of the locking assembly 20, in which the rotor 30 and thus the patient's leg can be rotated.

The locking functions as follows: multiple spring-loaded locking pins 32, which are arranged about the circumference of the rotor 30, are positioned opposite corresponding locking recesses 44 on the stator. The number and division of the recesses 44 and pins 32 are different, however. Because of this, none of the pins 32 and recesses 44 are ever opposite one another; however, one pin 32 of a group is always precisely opposite one recess 44 once the difference angle is exceeded. This enables a very precise engagement to be achieved, which is much less than the division of pins 32 and recesses 44. In the example shown, the pins 32 are each combined into groups, wherein the pattern repeats four times on the circumference so that always four pins 32 from the four different groups simultaneously engage and transfer the load.

The recesses 44 do not fully cover the cross-section of the locking pins 32 here, but instead the radially external region 32a of the pins is exposed. The release ring 50 uses precisely this external exposed region in order to carry the pins 32 along during the pullback of the star-shaped handle 22 and thus to release the locking. When the star-shaped handle 22 is released, the pins 32 can again move to the recesses 44 and four pins 32 then engage with the opposing recesses 44.

NUMERAL DESIGNATIONS

1 Operating table
2 Patient support surface
3 Column
4 Base
10 Extension bar
12 Bar
14 Movable strut
16 Spindle traction mechanism
18 Bracket for patient's foot
20 Locking assembly
22 Star-shaped handle
24 Interface
26 Scale ring
28 Handcrank
30 Rotor
32 Locking pin
32a Radially external section
34 Through-hole
36 Guide groove
38 Locking bush
40 Spring
42 Stator
44 Locking recesses
46 Guide groove
48 Spring
50 Release ring, release protrusion 52 Stop pin
L Longitudinal axis
P Patient

The invention claimed is:

1. A rotation assembly for connecting to an operating table for the purpose of rotating a patient's leg around its longitudinal axis, wherein the rotation assembly comprises:
an interface for attaching the foot of the patient's leg to the rotation assembly;
a rotor, to which the interface is connected in a torsionally resistant manner and which is operable to rotate the interface and thus the patient's leg about the longitudinal axis;
a stator, on which the rotor is rotatably mounted, such that the rotor can rotate relative to the stator;
a rotary handle for rotating the rotor; and
a locking assembly for blocking the rotation of the rotor relative to the stator,
wherein the rotary handle is mounted on the rotor so as to move the rotor around an axis of rotation, and
wherein the locking assembly is actuated by moving the rotary handle along the axis of rotation of the rotor in an axial direction away from the interface.

2. The rotation assembly according to claim 1, wherein the locking assembly has at least two groups of locking pins and a plurality of locking recesses, wherein the number of locking pins is different from the number of locking recesses.

3. The rotation assembly according to claim 2, wherein the rotor comprises multiple through-holes on an inner circumference, in which one of the locking pins of the at least two groups of locking pins is spring-loaded and pretensioned.

4. The rotation assembly according to claim 2, wherein the at least two groups of locking pins and the locking recesses each form a circular assembly.

5. The rotation assembly according to claim 2, wherein the at least two groups of locking pins and the locking recesses Oil) are each arranged symmetrically radially.

6. The rotation assembly according to claim 2, wherein, upon release of the locking assembly, all the locking pins are simultaneously pulled out of the locking recesses against a spring preload.

7. The rotation assembly according to claim 6, wherein the simultaneous pulling of all locking pins out of the locking recesses takes place by means of the movement of the rotary handle along the axis of rotation of the rotor.

8. The rotation assembly according to claim 7, further comprising a release ring, which has contact with the locking pins of the at least two groups of locking pins upon movement of the rotary handle along the axis of rotation.

9. The rotation assembly according to claim 8, wherein a respective section of the locking pins protrudes radially over the respective locking recess, and wherein the release ring has contact with this respectively protruding section upon movement of the rotary handle along the axis of rotation.

10. A rotation assembly for connecting to an operating table for the purpose of rotating a patient's leg around its longitudinal axis, wherein the rotation assembly comprises:
an interface for attaching the foot of the patient's leg to the rotation assembly;
a rotor, to which the interface is connected in a torsionally resistant manner and which is operable to rotate the interface and thus the patient's leg about the longitudinal axis;
a stator, on which the rotor is rotatably mounted, such that the rotor can rotate relative to the stator;
a rotary handle for rotating the rotor; and
a locking assembly for blocking the rotation of the rotor relative to the stator,
wherein the rotary handle is mounted on the rotor so as to move the rotor, and
wherein the locking assembly can be actuated by moving the rotary handle on the rotor, and
wherein the locking assembly can be locked in a release position, in which the rotor can be freely rotated relative to the stator.

11. The rotation assembly according to claim 10, wherein the locking assembly can be locked in the release position by pressing a button attached to the rotary handle.

12. The rotation assembly according to claim 11, wherein the rotary handle is a star-shaped handle with multiple handholds, each of which extends in the radial direction of the rotor, and wherein the button is arranged at one end of a handhold.

13. A rotation assembly for connecting to an operating table for the purpose of rotating a patient's leg around its longitudinal axis, wherein the rotation assembly comprises:
an interface for attaching the foot of the patient's leg to the rotation assembly;
a rotor, to which the interface is connected in a torsionally resistant manner and which is operable to rotate the interface and thus the patient's leg about the longitudinal axis;
a stator, on which the rotor is rotatably mounted, such that the rotor can rotate relative to the stator;
a rotary handle for rotating the rotor; and
a locking assembly for blocking the rotation of the rotor relative to the stator,
the locking assembly comprising a plurality of locking pins and a plurality of locking recesses each shaped to receive a locking pin,
wherein the locking assembly comprises different quantities of locking pins and locking recesses;
wherein the rotary handle is mounted on the rotor so as to move the rotor;
wherein the locking assembly is actuated by means of moving the rotary handle on the rotor;
wherein the locking assembly can be unlocked for rotation by axially moving the rotary handle such that all the locking pins are simultaneously pulled out of the locking recesses; and
wherein the plurality of locking pins comprises four groups of locking pins, wherein one of the respective locking pins of the four groups of locking pins is accommodated with one section completely in one of the respective locking recesses in order to block the rotational movement of the rotor.

14. The rotation assembly according to claim 13, wherein the rotary handle is axially moved along an axis of rotation of the rotor away from the interface.

15. The rotation assembly according to claim 14, further comprising a release ring, which has contact with the locking pins of the four groups of locking pins-upon movement of the rotary handle along the axis of rotation.

* * * * *